United States Patent
Rhoades et al.

(10) Patent No.: US 6,247,811 B1
(45) Date of Patent: Jun. 19, 2001

(54) MULTI-PURPOSE EYEWEAR

(75) Inventors: James Rhoades, Concord, CA (US); Sinjon Webb, Boulder, CO (US)

(73) Assignee: Xspex LLC, Lafayette, CA (US)

( * ) Notice: Subject to any disclaimer, the term of this patent is extended or adjusted under 35 U.S.C. 154(b) by 0 days.

(21) Appl. No.: 09/632,859

(22) Filed: Aug. 7, 2000

Related U.S. Application Data

(63) Continuation of application No. 09/264,460, filed on Mar. 8, 1999, now abandoned.

(51) Int. Cl.[7] .................................................. G02C 3/00
(52) U.S. Cl. .......................... 351/156; 351/43; 351/118; 2/431; 2/452
(58) Field of Search ................................ 351/43, 62, 111, 351/116–118, 119, 121, 156, 158; 2/426, 431, 436, 448, 450, 452

(56) References Cited

U.S. PATENT DOCUMENTS

| | | | |
|---|---|---|---|
| 2,066,838 | 1/1937 | Kimball | 2/452 |
| 2,526,181 | 10/1950 | Wilen | 351/41 |
| 2,545,428 | 3/1951 | Liautaud | 351/156 |
| 3,526,449 | 9/1970 | Salvage | 351/156 |
| 4,955,087 | 9/1990 | Perez et al. | 2/12 |
| 4,989,274 | 2/1991 | Patelski, III | 351/156 |
| 5,016,293 * | 5/1991 | Lickle | 2/436 |
| 5,129,109 * | 7/1992 | Runckel | 351/41 |
| 5,146,245 * | 9/1992 | Bolinger | 351/118 |
| 5,191,363 * | 3/1993 | Smith et al. | 351/62 |
| 5,265,165 * | 11/1993 | Rauch | 351/41 |
| 5,309,577 * | 5/1994 | Buononato et al. | 351/41 |
| 5,423,092 * | 6/1995 | Kawai | 351/41 |
| 5,488,411 * | 1/1996 | Pomatti | 351/41 |
| 5,711,035 * | 1/1998 | Haslbeck | 2/436 |
| 5,727,259 * | 3/1998 | Kawamata | 2/452 |
| 5,966,745 * | 10/1999 | Schwartz et al. | 2/428 |

FOREIGN PATENT DOCUMENTS

| | | | |
|---|---|---|---|
| 5-40247 * | 2/1993 | (JP) | 351/43 |
| WO 96/22752 * | 8/1996 | (WO) . | |

OTHER PUBLICATIONS http//:www.performance BUGZ LUNAZ GOGGLES.

* cited by examiner

*Primary Examiner*—Huy Mai
(74) *Attorney, Agent, or Firm*—Pillsbury Winthrop LLP

(57) ABSTRACT

The present multi-purpose eyewear uses a pliable frame and nose bridge in cooperation with strap adjustment and quick release mechanisms to enable multiple uses of the eyewear and adjustment of the eyewear while in place on the head of the wearer. The wraparound frames incorporate a sealant, such as a bonded gel filled rubber, around the lens periphery of the frame to present a comfortable interface between the wearer's skin and the eyewear. The strap adjustment and quick release mechanisms are simple to use and enable the eyewear to be adjusted while in place on the head of the wearer to fit the wearer in a manner to create a water-tight/air-tight seal (fluid-tight seal) around the wearer's eyes in a manner to conform to the contours of the wearer's face and avoid irritation of the skin from prolonged use. The lenses that are used in the eyewear are capable of being manufactured to prescription specifications and can include sunlight protection. The multi-purpose eyewear preferably also includes ear stems that are interchangeable with the strap to provide eyewear of conventional appearance when used as eyeglasses and/or sunglasses.

50 Claims, 6 Drawing Sheets

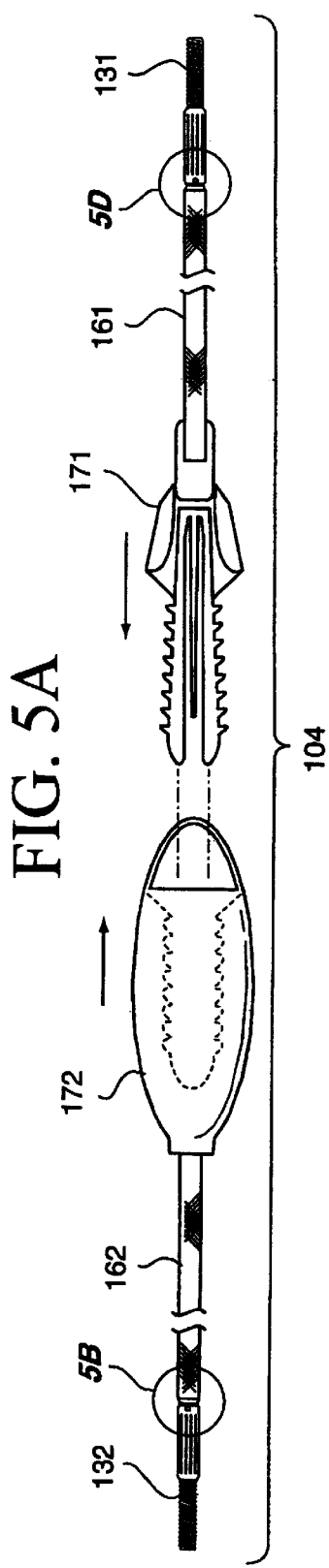
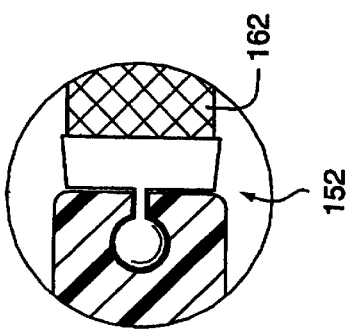
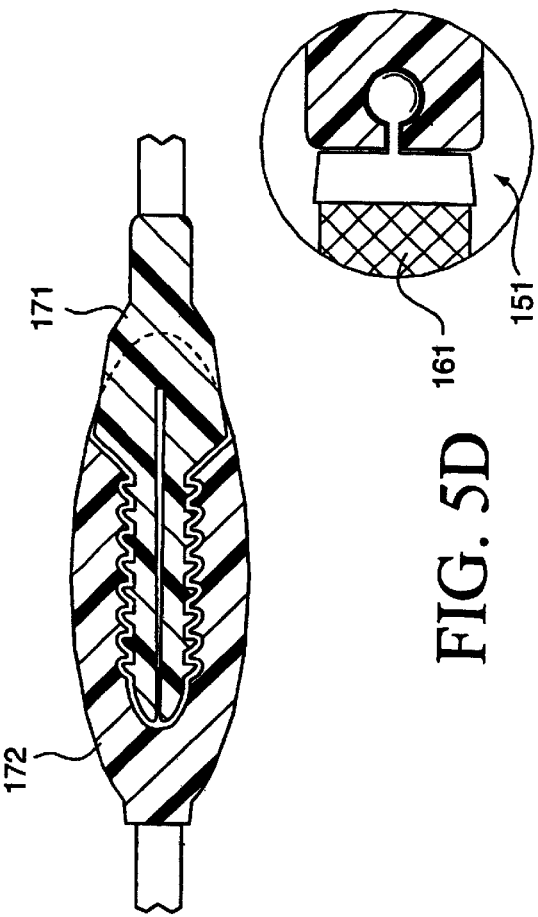

MULTI-PURPOSE EYEWEAR

This is a continuation of application Ser. No. 09/264,460 filed Mar. 8, 1999 now abandoned.

FIELD OF THE INVENTION

This invention relates to eyewear and in particular to eyewear that has multiple functions, including being usable as traditional eyeglasses, as air/water-tight goggles and as glasses that enable a controllable air flow around the lenses, with the lenses thereof also being capable of providing vision correction and/or sun protection for the wearer.

PROBLEM

It is a problem in the field of eyewear to provide the wearer with a product that has multiple uses. In particular, there are many endeavors in which the participant is preferably equipped with eyewear that protects the eyes from an ambient environment which can contain one or more hostile elements. These hostile elements can include, but are not limited to: water; water-borne chemicals; air flow; extremes of air temperature; air-borne particulates such as dust, dirt, smoke and the like; and sunlight. Traditional solutions of providing a wearer with basic eye protection from sunlight and a modicum of hostile elements comprise a rigid eyeglass frame that is secured in place on the wearer's face by means of a strap. This solution is largely ineffective to provide the user with protection from the more hostile conditions, since the rigid eyeglass frame does not enclose the wearer's eyes and enables the hostile elements to impact the wearer's eyes. One advantage of the rigid eyeglass frame is that the lenses can be manufactured to provide the user with vision correction capability as well as sunlight protection.

An alternative solution to protect the wearer's eyes is to manufacture the eyeglass frame of a flexible material such that it is conformable to the wearer's face by the application of tension to the frame via a flexible strap. The flexible strap pulls the eyeglass frame against the wearer's face to provide an air/water-tight seal between the eyeglass frame and the wearer's skin. Neoprene and foam rubber are the materials used to form the seal but can cause skin irritation and do not adequately shape to the individual's facial contours. Furthermore, these flexible eyeglass frames typically use the eye socket as a point of contact which can constrict blood circulation in this area and result in bruising of the skin. Therefore, eyewear that provide eye socket contact cannot be used for an extended periods of time. Finally, these goggles do not provide vision correction and must be worn over prescription eyeglasses or in place of prescription eyeglasses in most applications. This causes the wearer to lose the vision correction provided by the prescription eyeglasses and the wearer must carry multiple pairs of eyewear: prescription eyeglasses, goggles, sunglasses, and the like, which is inconvenient at best. Examples of typical eyewear are found in numerous patents that have addressed this issue.

U.S. Pat. No. 2,526,181 issued to Wilen discloses underwater goggles that are formed of a frame manufactured of a material which is compressible against the user's face in a manner to be impervious to water and formed to fit around the user's eyes. The frame has a recess adjacent its front edge for receiving a single piece of plate glass and two attachment points for receiving the ends of a flexible band which is adjustable to place a compression force on the frame to form the watertight seal between the frame and the user's skin. These underwater goggles are a single purpose device, somewhat uncomfortable to wear for an extended period of time, must be worn over prescription eyeglasses, and are inapplicable to other than the underwater environment.

U.S. Pat. No. 3,526,449 issued to Bolle et al discloses one piece sunglasses that comprise a single molded piece that includes two lenses and the supporting frame as an integral unit. The lenses are concavo-convex, separated by a bridge portion, with each lens terminated laterally in an elongated rearward extension that is flexible and conformable to the head of the user. These sunglasses provide some protection to the wearer but do not provide a water-tight or air-tight seal for the eyes of the wearer.

U.S. Pat. No. 4,989,274 issued to Patelski III discloses sports goggles that comprise a frame having left and right vision openings and having anterior and posterior surfaces. Right and left lenses are sized and shaped to cover the respective vision openings. The frame is constructed of a flexible material to enable the posterior portion to conform the user's face. An air gap is maintained between the lenses and the frame to enable air circulation there between to prevent fogging of the lenses. The frame includes a flexible adjustable strap to secure the frame to the user's head. These sports goggles provide some protection to the wearer but do not provide a water-tight or air-tight seal for the eyes of the wearer. U.S. Pat. No. 5,129,109 issued to Runckel discloses swim goggles that include an inflatable air gasket seal. The goggles have two eye pieces, each of which includes a frame that extends continuously around a lens opening. An inflatable cushion member is provided for each eyepiece and extends throughout the frame portion of the eyepiece. The frame includes a flexible adjustable strap to secure the frame to the user's head. These swim goggles are a single purpose device, somewhat uncomfortable to wear for an extended period of time, must be worn over prescription eyeglasses, and are inapplicable to other than the underwater environment.

U.S. Pat. No. 5,265,165 issued to Rauch discloses an audio headwear that produces sound output in addition to providing the visor or headband function. The audio headwear comprises a flexible frame, a protective layer and two speaker elements. The speakers are attached between the flexible frame and the protective layer that is attached to cover the bottom side of the visor. The speaker elements therefore do not interfere with the visor yet provide an audio output that can be heard by the wearer. This headwear does not address the problem of providing a water-tight or air-tight seal for the eyes of the wearer and cannot incorporate prescription lenses for vision correction.

U.S. Pat. No. 5,309,577 issued to Buononato et al discloses buoyant wraparound sunglasses that comprise an elongated flexible strap that has its ends terminated by fasteners that are joinable to form a band. The strap has a cutout section adapted to receive an eye shield. These sunglasses provide some protection to the wearer but do not provide a water-tight or air-tight seal for the eyes of the wearer and cannot incorporate prescription lenses for vision correction.

U.S. Pat. No. 5,423,092 issued to Kawai discloses eyewear that can be switched to function either as a pair of sunglasses or goggles. The eyewear combines a frame member and a lens member that function as sunglasses. The eyewear can be converted to goggles by replacing the frame member with an upper goggle frame member and the addition of a detachable lower goggle frame. While this eyewear provided a dual purpose, the lens is clear glass and does not provide vision correction. This eyewear must be worn over the wearer's prescription eyeglasses, if possible, and are complex to disassemble and reassemble.

U.S. Pat. No. 5,488,441 issued to Pomatti discloses an adjustable eyeglasses retainer. The eyeglass frame is fabricated of a combination of a semi-rigid lens retaining support and a semi-flexible nose bridge and semi-flexible temple brows has having a retaining strap removably engagable around the back of the head. Closed cell shaped padding is applied to the lens supports facing the eye sockets to protect the eyes from the elements. These eyeglasses provide some protection to the wearer but do not provide a water-tight or air-tight seal for the eyes of the wearer Thus, in the field of eyewear, there is a need for eyewear that can be effectively used as either eyeglasses - unsealed with free flow of air around the lenses or air-tight/water-tight goggles. This eyewear should be convenient to use, simple to adapt to multiple uses, and simply adjustable when on the wearer's head to fit a wide range of sizes and shapes of heads. Unfortunately, such eyewear is presently not available.

SOLUTION

The above described problems are solved and a technical advance achieved in the field of eyewear by the present multi-purpose eyewear that uses a pliable frame and nose bridge in cooperation with strap adjustment and quick release mechanisms to enable multiple uses of the eyewear and adjustment of the eyewear while in place on the head of the wearer. The wraparound frames incorporate a sealant, such as a bonded gel filled rubber, around the lens periphery of the frame to present a comfortable interface between the wearer's skin and the eyewear. The strap adjustment and quick release mechanisms are simple to use and enable the eyewear to be adjusted while in place on the head of the wearer to fit the wearer in a manner to create a water-tight/air-tight seal (fluid-tight seal) around the wearer's eyes in a manner to conform to the contours of the wearer's face and avoid irritation of the skin from prolonged use. The lenses that are used in the eyewear are capable of being manufactured to prescription specifications and can include sunlight protection. The multi-purpose eyewear preferably also includes ear stems that are interchangeable with the strap to provide eyewear of conventional appearance when used as eyeglasses and/or sunglasses.

The multi-purpose eyewear can be used by a vast number of athletes who participate in any water sport or active land sport, from surfers to skydivers to triathletes. The multi-purpose eyewear is for use above and under water as well as through air and on land. The frame is composed of a pliable material that is conformable to the contours of the human face. The frame functions both to position the lenses in front of the wearer's eyes and to seal the lenses against the wearer's head in a watertight manner. The wraparound frames incorporate a bonded gel filled rubber sealant around the lens periphery of the frame to present a comfortable interface between the wearer's skin and the eyewear. The gel seal rests on the bones that surround the eye socket instead of in the eye socket and retains its original shape when removed from the wearer. Temple mounts are provided in the frame and comprise horizontal screw-in turnbuckles that screw into the temple mounted horizontal screw fitting on one end and a strap on the other end. The strap is connected to an adjustment mechanism, such as a turnbuckle screw with a free spinning swivel, that is crimped to a cord, which can be either elastic or ridged to facilitate adjustment of the strap. The user can turn the independent turnbuckles to cause the cord to pull the glasses toward the user's face without twisting the strap. A zip clip is optionally provided in the strap to provide a size adjustable quick release clip that is typically centered on the back of the wearer's head and is used to perform the preliminary fit to pull the frame toward the wearers face. The turnbuckle system is then used to fine adjust and to seal the goggles to the wearer's face or maintain the frames without tension for an unsealed fit on the wearer's head, to enable a controllable amount of air flow around the lenses. The turnbuckles permit independent adjustment from one temple to the other if the wearer's face is not uniform from side to side. When the wearer does not require goggles, the strap can be simply removed and replaced with folding ear stems that screw into the temple mounted screw sockets to provide the user with the option of wrap around eyeglasses. The lenses can be any lenses known in the field of specialty, including prescription or plain glass with the user being able to use the prescription lenses with the frame in both a conventional eyeglasses mode or in a watertight goggle mode. The goggles are simply vented to enable air flow to the eyes due to the use of the flexible frames, since the frames return to their initial shape as the tension is released and the frames flex away from the wearer's face.

BRIEF DESCRIPTION OF THE DRAWING

FIGS. 5A-5D illustrate additional details of the quick release and turnbuckle mechanisms of the strap of the present multi-purpose eyewear;

DETAILED DESCRIPTION

Figure 1:
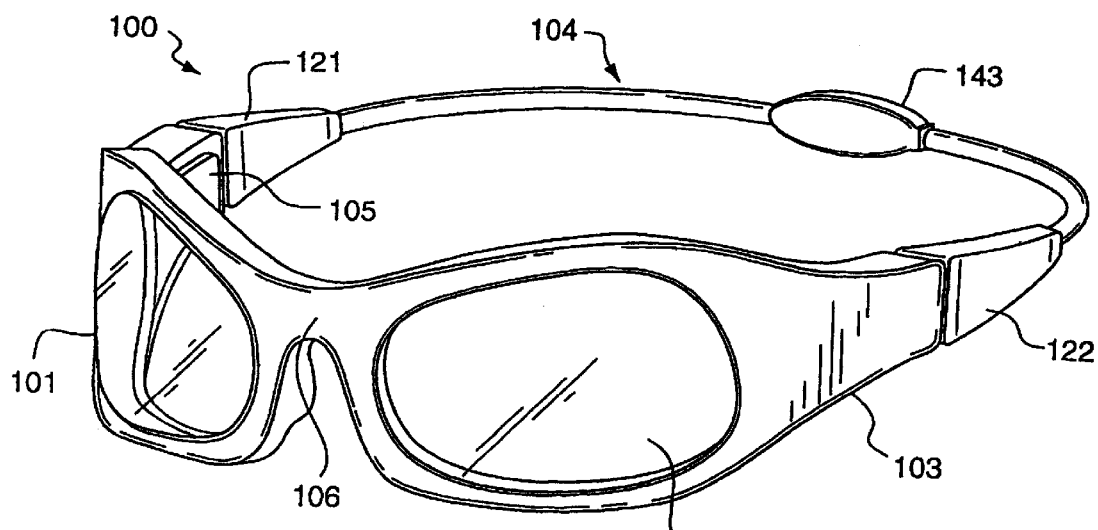
FIG. 1 illustrates a perspective view of the present multi-purpose eyewear as equipped with a strap.
Figure 2:
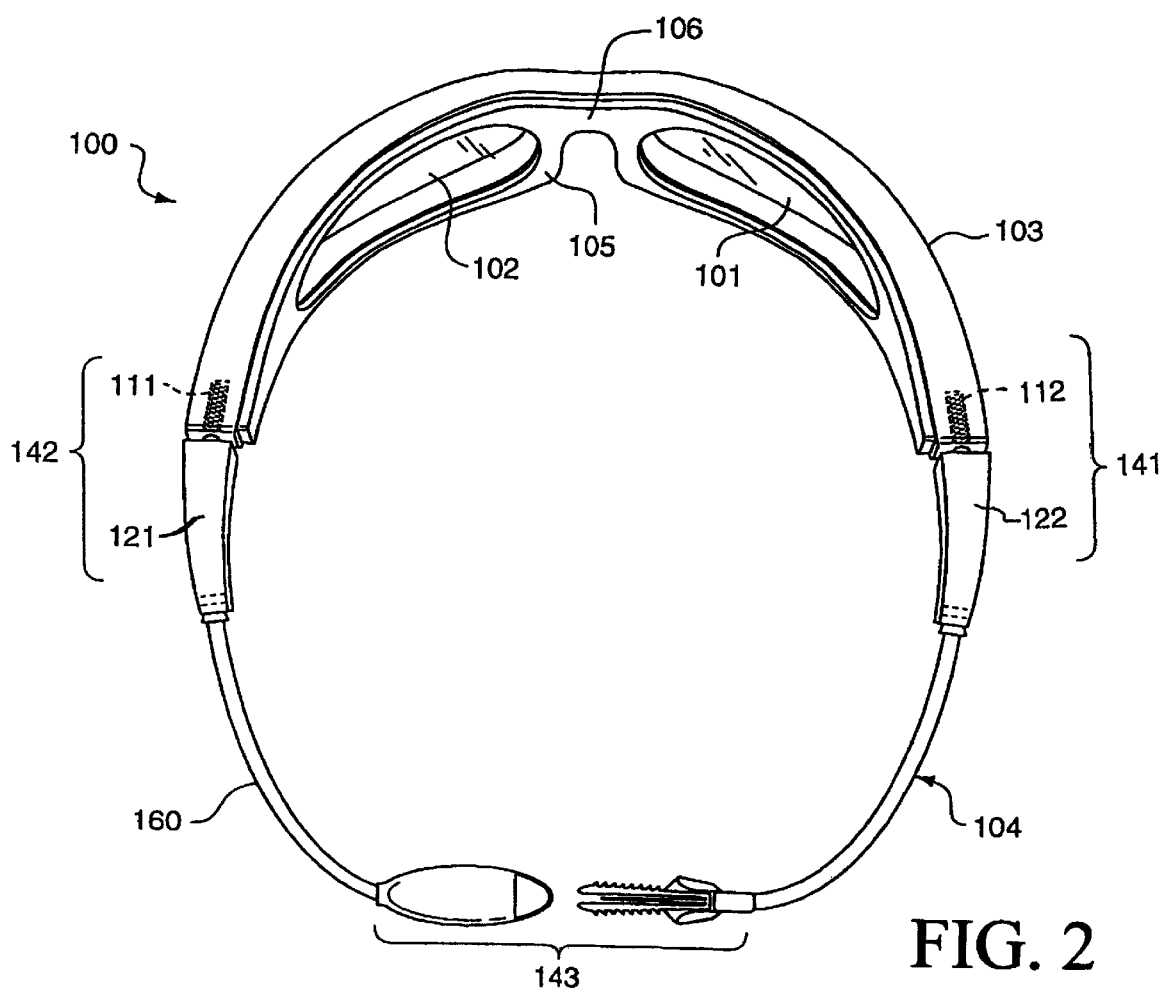
FIG. 2 illustrates a top plan view of the present multi-purpose eyewear as equipped with a strap.

FIG. 1 illustrates a perspective view and FIG. 2 illustrates a top plan view of the present multi-purpose eyewear as equipped with a strap. The multi-purpose eyewear 100 comprises first 101 and second 102 lenses, a pliable wraparound frame 103 and an adjustable strap 104. The wraparound frame 103 incorporates a bonded gel filled rubber sealant 105 around the lens periphery of the pliable wraparound frame 103 to present a comfortable interface between the wearer's skin and the multi-purpose eyewear 100. The strap 104 is equipped with fine adjustment 141, 142 and quick release 143 mechanisms that are simple to use and enable the multi-purpose eyewear 100 to be adjusted to fit the wearer in a manner to create a water-tight/air-tight seal around the wearer's eyes in a manner to both conform to the contours of the wearer's face and avoid irritation of the skin from prolonged use. The lenses 101, 102 that are used in the multi-purpose eyewear 100 are capable of being manufactured to prescription specifications and can include sunlight protection. The multi-purpose eyewear 100 preferably also includes ear stems 301, 302 (FIG. 3) that are interchangeable with the strap 104 to provide eyewear of conventional appearance when used as eyeglasses and/or sunglasses.

Frame and Lenses

Figure 6:
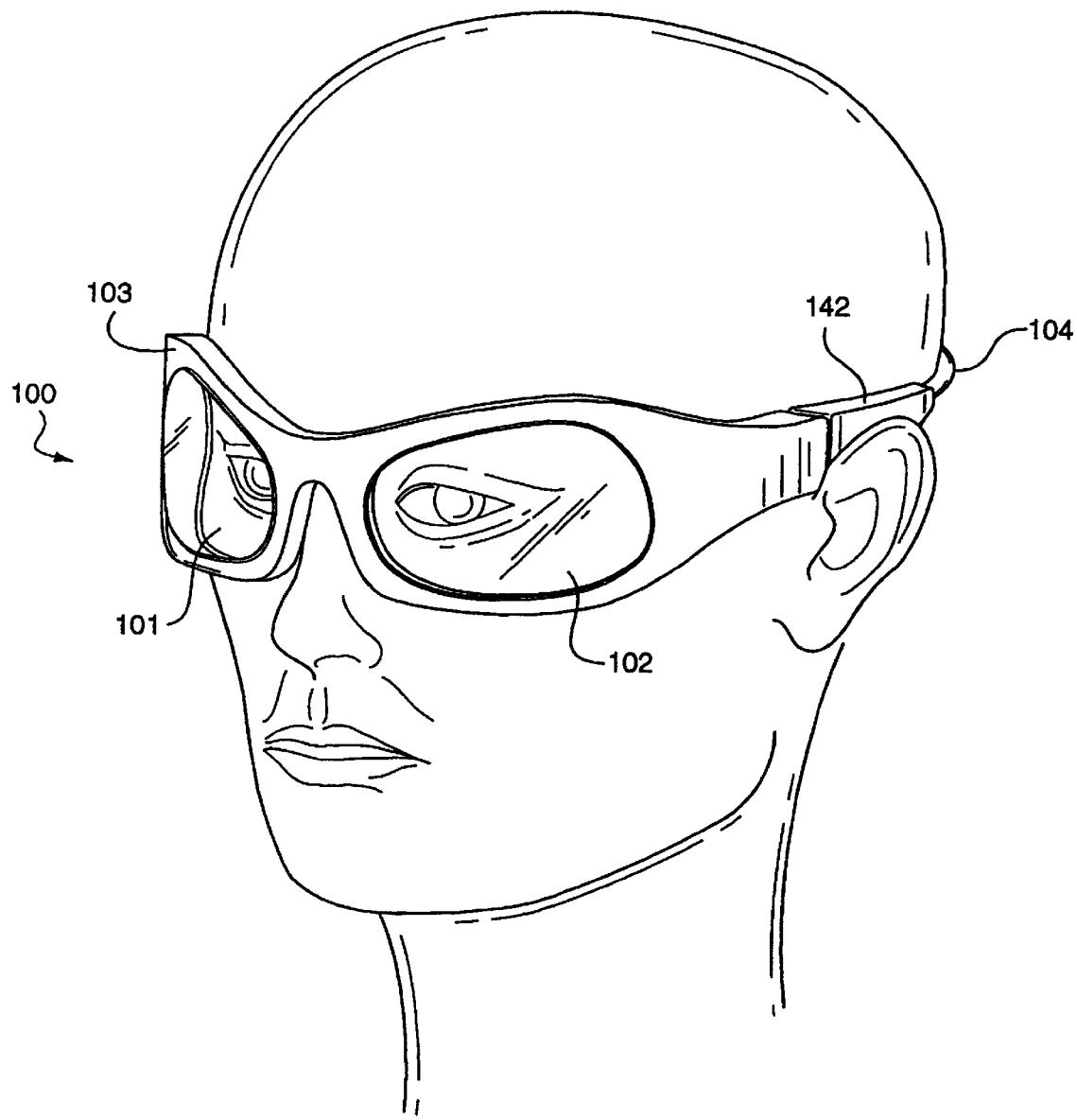
FIG. 6 illustrates a left front perspective view of the present multi-purpose eyewear as equipped with a strap and worn by a user.
Figure 7:
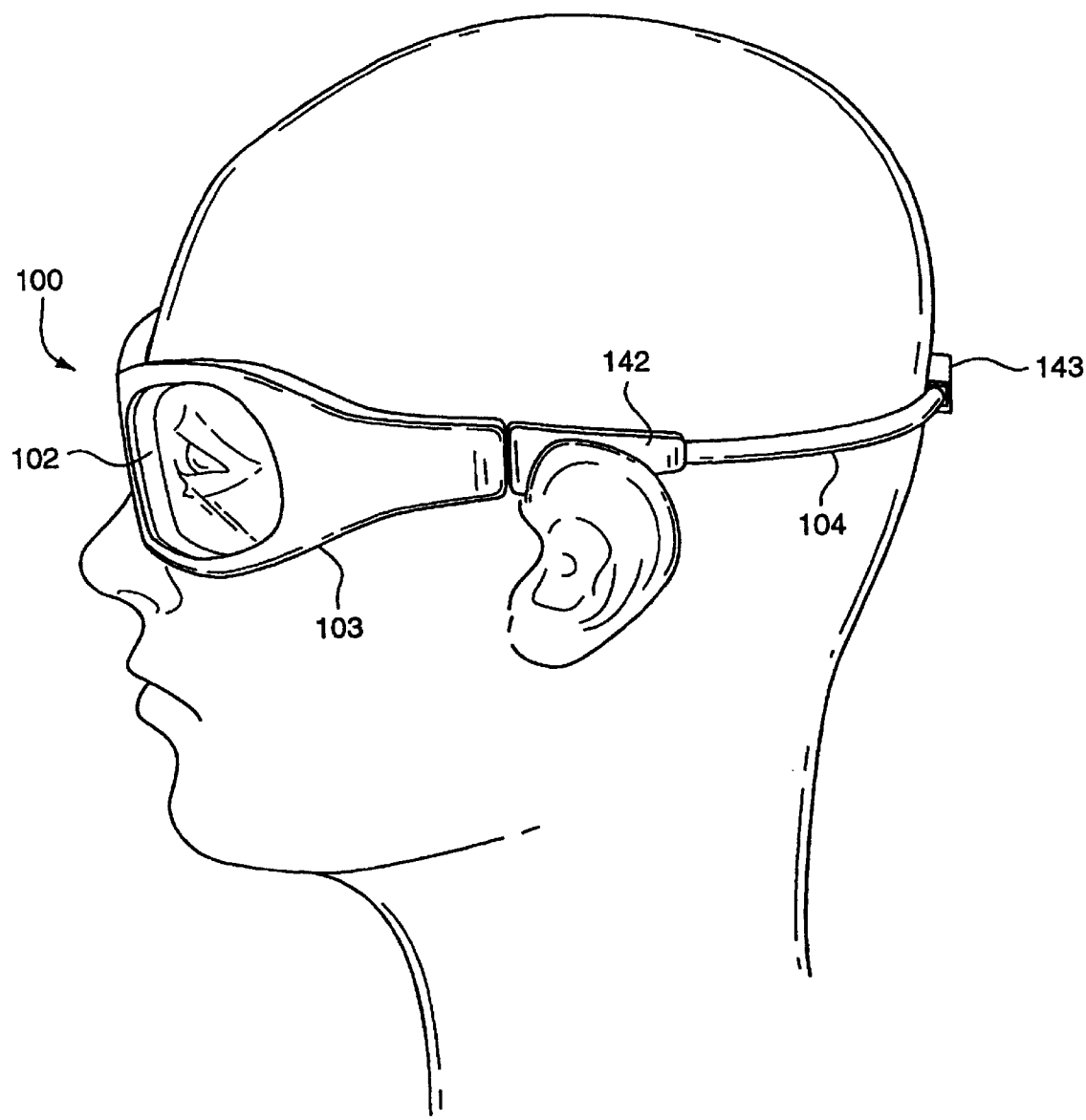
FIG. 7 illustrates a left side perspective view of the present multi-purpose eyewear as equipped with a strap and worn by a user.
Figure 8:
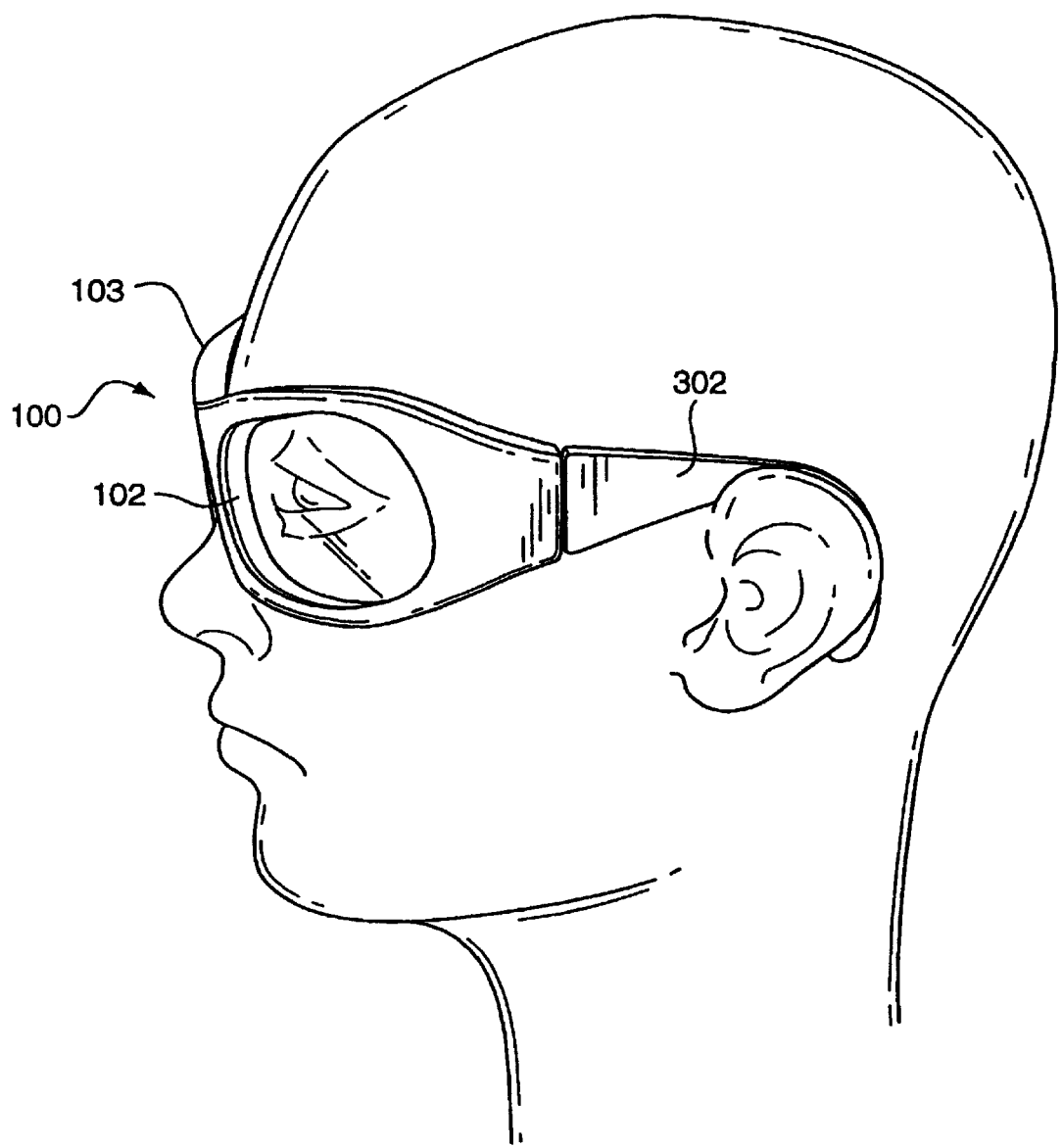
FIG. 8 illustrates a left side perspective view of the present multi-purpose eyewear as equipped with ear pieces and worn by a user.

To further illustrate the multi-purpose eyewear, FIGS. 6–7 illustrate left front and left side perspective views of the present multi-purpose eyewear as equipped with a strap and worn by a user, while FIG. 8 illustrates a left side perspective view of the present multi-purpose eyewear as equipped with ear pieces and worn by a user. The frame 103 is composed of a pliable material that is conformable to the contours of the human face. The frame 103 functions both to position the lenses 101, 102 in front of the wearer's eyes and to seal the lenses 101, 102 against the wearer's head in a watertight manner when the multi-purpose eyewear 100 is used as goggles. The frame materials are selected to be rugged, not flimsy, yet stylish for conventional wear when the multi-purpose eyewear 100 is used as eyeglasses. The frame 103 includes a nose bridge 106 that joins the lenses 101, 102 together and is concave shaped to conform to the shape of the wearer's nose. The nose bridge 106 can be formed of a material that is bendable into the sides of the nose where the nose meets the eye socket to create a seal when the strap fine adjustment 141, 142 and quick release 143 mechanisms are tightened to form goggles. The frame 103 can optionally include a plurality of holes 107 formed therein to provide an anti-fogging capability for the multi-purpose eyewear 100.

The wraparound frames 103 incorporate a bonded gel filled rubber seal 105 located around the lens periphery of the frame 103 to present a comfortable interface between the wearer's skin and the eyewear. The gel filled seal 105 consists of a housing of a rubber-like material that encloses an interior space, which is filled with a gel that is deformable. The gel filled seal 105 retains its original shape when removed from the wearer and is conformable to any wearer's facial contours. The gel filled seal 105 rests on the bones that surround the eye socket instead of resting in the eye socket to thereby provide a significant improvement in comfort for the wearer. The gel filled seal 105 can be manufactured of commercially available materials, such as the Aviation headset design by Bose® and presents a comfortable interface between the wearer's skin and the mutli-purpose eyewear.

The lenses 101, 102 can be any lenses known in the field of specialty, including prescription or plain glass with the user being able to use the prescription lenses with the frame 103 in both a conventional eyeglasses mode or in a watertight goggle mode. The goggles are simply vented to enable air flow to the eyes due to the use of the gel filled seal 105, since the frames 103 return to their initial shape as the tension is released and the frames 103 and gel filled seal 105 flex away from the wearer's face. Photo chromatic lenses can be used to enable the user to avail themselves of the light sensitive properties of this material.

The frames 103 also provide ample room for the wearer's eyelashes for unhindered eyelash movement due to the use of the gel filled seal 105. A proper sealed fit included for goggles includes an unrestricted eyelash movement when the eyewear is sealed to the face as well as a seal on the bones around the eye socket, rather than a seal in the eye socket.

Goggles Application of the Multi-Purpose Eyewear

Temple mounts 111, 112 are provided in the frame 103 at locations adjacent the lens apertures, at the far side of each lens aperture from the nose bridge 106. The temple mounts 111, 112 comprise horizontal screw fittings mounted into the body of the frame 103 and that screw into one end of a horizontal screw-in turnbuckle 121, 122. For a goggle application of the multi-purpose eyewear 100, the turnbuckles 121, 122 are attachable at the other end to screw fittings 131, 132 that terminate the ends of the strap 104, which strap 104 extends around the back of the wearer's head to interconnect the two temple mounts 111, 112. The strap 104 makes use of an elastic cord 160 to generate a tension on the temple mounts 111, 112 to thereby force the frame 103 against the wearer's face with a controllable amount of force. The elastic cord 160 is connected to a turnbuckle screw 131, 132 with a free spinning swivel 151, 152 that is crimped to a flexible elastic cord 160. The user can turn the independent turnbuckles 121, 122 to cause the elastic cord 160 to generate an increased tension on the temple mounts 111, 112 to pull the glasses toward the user's face without twisting the strap 104. A quick release clip 143 is provided in the strap 104 to provide a size adjustable quick release clip that is typically centered on the back of the wearer's head and is used to perform the preliminary fit to pull the frame 103 toward the wearers face. The turnbuckle system 121, 122 is then used to fine adjust and to seal the goggles to the wearer's face. The turnbuckles 121, 122 permit independent adjustment from one temple to the other if the wearer's face is not uniform from side to side. The strap 104 is adjustable for an unsealed free airflow configuration to a sealed fluid-tight configuration. The elastic cord 160 can be a single piece that is length adjustable or, preferably the two segments of elastic cord 161, 162 shown in FIG. 2.

Eyeglasses Application of the Multi-Purpose Eyewear

Figure 3:
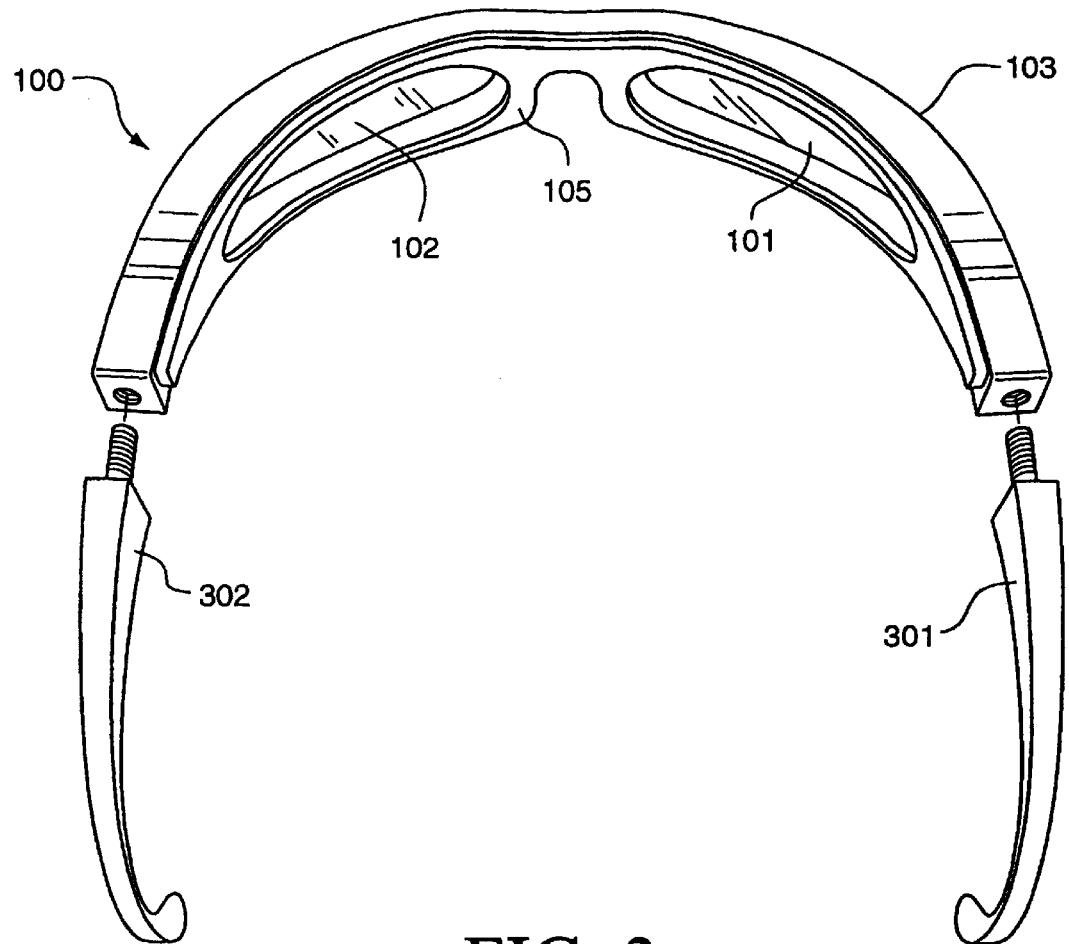
FIGS. 3 and 4 illustrate top plan and side plan views respectively, of the present multi-purpose eyewear as equipped with ear pieces.
Figure 4:
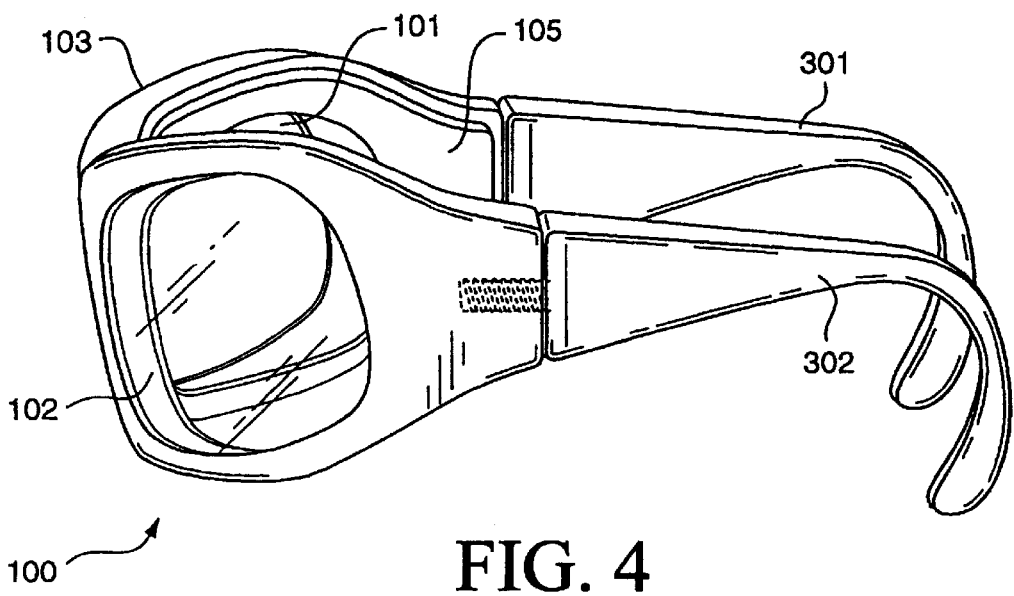

When the wearer does not require goggles, the strap 104 can be simply removed by unscrewing the turnbuckles 121, 122 and replacing the strap 104 with folding ear stems 301, 302 that screw into the temple mounted screw sockets 111, 112 to provide the user with the option of wrap around eyeglasses. FIGS. 3 and 4 illustrate top plan and side plan views respectively, of the present multi-purpose eyewear 100 as equipped with ear pieces 301, 302. In the case of prescription lenses 101, 102, the proper selection of the size of earpieces 301, 302 and the adjustments made to strap 104 to implement goggles, the focal length of the lenses 101, 102 do not change significantly and the wearer is afforded the benefit of prescription glasses in both the eyeglass mode and the goggles mode. This enables the wearer to have a single piece of eyewear that serves multiple functions.

Quick Release and Turnbuckle Mechanisms

FIGS. 5A–5D illustrate additional details of the quick release 160 and turnbuckle 121, 122 mechanisms of the strap 104 of the present multi-purpose eyewear 100. The temple mounts 111, 112 to the frame 103 are shown as attachable to horizontal screw-in turnbuckles 121, 122. Turnbuckles 121, 122 use a threaded sleeve to pull two opposing screws 111, 112 and 131, 132 toward each other for tightening. The turnbuckles 121, 122 screw into the temple mounted horizontal screw fitting 111,112 on one end and are attachable at the other end to screw fittings 131, 132 that terminate the ends of the two segments 161, 162 of strap 104. The strap 104 is connected to the turnbuckle 121, 122 with a free spinning swivel 151, 152 that is crimped to the flexible elastic cord 160. The flexible elastic cord 160 can be any suitable elastic cordage or webbing and can for example be a ¼ inch bungee cord.

The quick release clip 143 portion of the strap 104 is a size adjustable quick release clip that is typically centered on the back of the wearer's head. The quick release clip 143 provides a second adjustment mechanism for fitting the multi-purpose eyewear 100 on the wearer's head when they are loose enough to allow free air flow about the eyes. The quick release clip 143 is used to perform the preliminary fit to pull the frame 104 toward the wearer's face. The turnbuckle 121, 122 system is then used to fine adjust and to seal the goggles to the wearer's eye bones. The turnbuckles 121, 122 permit independent adjustment from one temple to the other if the wearer's face is not uniform from side to side. The quick release clip 143 can be a male adapter 171 with a predetermined number of teeth, oriented in single file evenly spaced opposing dispositions attached to one end of a first segment 161 of the elastic cord 160. These teeth click into a mating female adapter 172 with slots provided for the teeth as they slide in, which female adapter 172 is attached to a first end of the second segment 162 of the elastic cord 160. The wearer releases the quick release clip 143 by simply squeezing the retractor button for the teeth and slides the male connector 171 to the desired position or separates the two sections of the strap 104 from each other. In this manner the distance between the respective first ends of the two segments 161, 162 of the elastic cord 160 can be precisely controlled and the tension produced by the elastic cord 160 on the frame 103 can be incrementally increased or reduced.

The strap adjusting mechanisms can be any detachable mechanism and the turnbuckle mechanism 121, 122 is illustrated as a convenient and simple detachable mechanism that provides a wide range of adjustment. The strap adjusting mechanisms devices can alternatively comprise screws with swivels or universal joints attached to the strap. Rivet snaps, hook and loop fastener and clip-ins can also be used, as can tri slide webbing belt adjusters with quick release clips. Spring loaded sleeves or channels with locking adjust capabilities or encased bevel gears that lock with cogs and are releasable can also be used as alternative implementations of the strap adjusting mechanisms. Even a sheave system built into the temple mount that enables the user to slide an end of an attached strap to be adjusted with a sliding tension sleeve can perform the necessary strap adjusting function. The selection of the particular strap adjusting mechanisms used in the multi-purpose eyewear 100 is a matter of both engineering choice and economics and such choice is well within the skill of one familiar with this technology.

Summary

Thus, the present multi-purpose eyewear uses a pliable frame and nose bridge in cooperation with strap adjustment and quick release mechanisms to enable the use of the eyewear as either eyeglasses or goggles. The wraparound frames incorporate a bonded gel filled rubber sealant around the lens periphery of the frame to present a comfortable interface between the wearer's skin and the eyewear. The strap adjustment and quick release mechanisms are simple to use and enable the eyewear to be adjusted to fit the wearer in a manner to create a water-tight/air-tight seal around the wearer's eyes in a manner to conform to the contours of the wearer's face and avoid irritation of the skin from prolonged use. All adjustments can be made while on the head of the wearer.

What is claimed:

1. Multi-purpose eyewear for use by a wearer for multiple uses, including eyeglasses or goggles that provide a fluid tight seal of said multi-purpose eyewear about the wearer's eyes, comprising:

lenses for providing an element for the wearer to see through;

a convertible frame forming two lens apertures that receive said lenses for positioning said lenses in front of the eyes of said wearer, said two lens apertures being juxtaposed to each other and interconnected by a nose bridge;

a seal attached to said frame and located around a periphery of said two lens apertures for establishing a fluid-tight seal of said multi-purpose eyewear about the wearer's eyes; and a strap having a length dimension and first and second ends that are respectively attachable to said frame at respective locations adjacent said two lens apertures and distal from said bridge, said strap including a cord for generating a tension at said respective locations to pull said frame against said wearer's head in response to said cord being stretched around the wearer's head;

at least two strap length adjustment mechanisms attached to said cord for controllably adjusting said tension by varying said length dimension of said strap.

2. A goggle and an eyeglass combination eyewear, comprising:

a frame having a nose bridge, a pair of lens apertures, and a sealant around a periphery of each lens aperture;

a pair of strap release mechanisms removably connected one each to a left and a right end of said frame;

a strap mounted between said pair of strap release mechanisms; and a pair of ear stems interchangeable with said pair of strap release mechanisms;

wherein said frame is pliable and has an unsealed fit on a wearer's head until said frame is tensioned.

3. The eyewear of claim 2, wherein the sealant is a gel based fluid tight sealant comfortable to a user's face while under said tension, thereby creating a water tight seal and a controllable air flow seal.

4. The eyewear of claim 2, wherein said pair of release mechanisms each further comprise a female threaded socket in said frame end coupled with a threaded bolt of said release mechanism, thereby providing a fine tuning adjustment for said frame.

5. The eyewear of claim 4, wherein said release mechanism further comprises a cylindrical female connector around the threaded bolt, thereby providing a turnbuckle type tension adjust mechanism suitable for use while on the user.

6. The eyewear of claim 5, wherein the female connector further comprises a swivel connection to the strap, thereby providing a conformable fitting of the frame against a user's face.

7. The eyewear of claim 5, wherein the strap further comprises a combination tension adjust and quick release mechanism.

8. The eyewear of claim 4, wherein each ear stem further comprises a threaded bolt screwball into the female threaded sockets of the frame.

9. The eyewear of claim 2, wherein the strap further comprises a combination tension adjust and quick release mechanism.

10. The eyewear of claim 9, wherein the combination tension adjust and quick release mechanism further comprises a female receptacle having a hole with a plurality of notches, and a male connector having a pair of juxtaposed jaws having a common pivot, each jaw having a plurality of teeth matching said notches, wherein a user's squeeze of the jaws forms an adjustable mode of the male connector to provide an insertion and an adjustment of depth into said female receptacle hole, and a cessation of said squeeze provides a locking mode of the male connector with a meshing of the teeth in the notches.

11. Eyewear comprising:

a lens for the wearer to see through;

a convertible frame having a lens aperture that receives the lens and positions the lens to be in front of an eye of the wearer, the frame being freely deformable from a first untensioned position in which the lens aperture is spaced apart from the wearer's face to admit airflow therebetween and function as part of at least one of sunglasses and eyeglasses, to a second tensioned position in which the frame contacts the wearer's face to form a fluid-tight seal thereagainst to function as part of goggles, and at least one position intermediate the first and second positions; and a plurality of tensioning devices to selectively apply tension to cause the frame to deform from the first position to one of the other positions.

12. The eyewear of claim 11, wherein the tensioning device is to selectively cause the frame to move from one of the positions to be set in another one of the positions while the eyewear is on the wearer's head.

13. The eyewear of claim 11, wherein the tensioning device is to selectively cause the frame to move from one of the positions to be set in another one of the positions without disassembling the eyewear.

14. The eyewear of claim 11, wherein:

in the first position the frame permits airflow between itself and the wearer's face;

in the at least one intermediate position the frame permits a reduced amount of airflow relative to the first position; and in the second position the frame prevents airflow between itself and the wearer's face.

15. The eyewear of claim 11, wherein the seal is an airtight seal.

16. The eyewear of claim 15, wherein the seal is a watertight seal.

17. The eyewear of claim 11, further comprising:

another lens for the wearer to see through;

wherein the frame has another lens aperture that receives the another lens and positions the another lens to be in front of an eye of the wearer, the two lens apertures being juxtaposed to each other and interconnected by a nose bridge.

18. The eyewear of claim 11 wherein the lens provides vision correction capability for the wearer.

19. The eyewear of claim 11 wherein the lens provides sunlight protection capability for the wearer.

20. The eyewear of claim 11, wherein the frame comprises a sealing pad attached to the frame and located around a periphery of the lens aperture to establish the seal of the frame with the wearer's face.

21. The eyewear of claim 20, wherein the sealing pad is attached to a frontal surface of the frame most proximate to the wearer's face.

22. The eyewear of claim 20, wherein the sealing pad comprises:

a housing of a flexible material to conform to an irregular surface, the housing enclosing an interior space; and a gel filling the interior space of the housing and being deformable in response to forcing the housing against the wearer's face for conforming to the wearer's face.

23. The eyewear of claim 11, wherein the tensioning device comprises a strap having a length dimension and an end selectively attachable to and detachable from a mount on the frame, the strap including:

a cord to generate a tension on the frame to cause the frame to deform into one of the positions in response to the cord being stretched around the wearer's head; and a strap length adjustment device attached to the cord to controllably adjust the tension by varying the length dimension of the strap.

24. The eyewear of claim 23, wherein:

there are a plurality of the intermediate positions; and the cord is to controllably generate a continuously variable tension on the frame to cause the frame to set in one of the intermediate positions.

25. The eyewear of claim 23 wherein the strap further includes a connector attached to an end of the strap to releasably interconnect with the mount.

26. The eyewear of claim 25, wherein:

the strap has two ends selectively attachable to and detachable from the frame;

the frame further comprises another mount to releasably attach the strap to the frame; and the strap further includes another connector attached to an opposite end of the strap to releasably interconnect with the another mount.

27. The eyewear of claim 26, wherein:

the adjustment device includes two portions each to controllably vary the length of the strap and to connect a respective one of the mounts to a corresponding one of the connectors; and the two portions are operable independently of one another.

28. The eyewear of claim 25 wherein the adjustment device is to controllably vary the length of the strap and to connect the connector to the mount.

29. The eyewear of claim 28, wherein:

the adjustment device includes at least one of a screw and a threaded screw hole; and the frame includes at least one of a threaded screw hole and a screw to respectively mate with the at least one of the screw and threaded screw hole.

30. The eyewear of claim 28, wherein the adjustment device includes at least one turnbuckle.

31. The eyewear of claim 23, wherein:

the cord comprises first and second sections; and the adjustment device is to controllably vary the length of the strap by interconnecting an end of the first length of cord to an end of the second length of cord by a controllable varying distance.

32. The eyewear of claim 23 wherein the adjustment device is to controllably vary the length of the strap by varying a length of the cord.

33. Multi-purpose eyewear capable of providing an airtight seal about a wearer's eye, the eyewear comprising:

a lens for the wearer to see through;

a frame having a lens aperture that receives the lens and positions the lens to be in front of an eye of the wearer, the frame being deformable from a first untensioned position for using the eyewear as at least one of sunglasses and eyeglasses, and a second tensioned position for using the eyewear as goggles;

a seal attached to the frame and located around a periphery of the lens aperture to establish an air-tight seal of the multi-purpose eyewear about the eye in the second position; and a strap having a length dimension and an end selectively attachable to and detachable from the frame, the strap including
a cord to generate a tension on the frame to pull the frame against the wearer's head in response to the cord being stretched around the wearer's head, and
a plurality of strap length adjustment devices attached to the cord to controllably adjust the tension by varying the length dimension of the strap.

34. The multi-purpose eyewear of claim 33, further comprising:
another lens for the wearer to see through;
wherein the frame has another lens aperture that receives the another lens and positions the another lens to be in front of an eye of the wearer, the two lens apertures being juxtaposed to each other and interconnected by a nose bridge.

35. The multi-purpose eyewear of claim 33 wherein the lens provides vision correction capability for the wearer.

36. The multi-purpose eyewear of claim 33 wherein the lens provides sunlight protection capability for the wearer.

37. The multi-purpose eyewear of claim 33 wherein the seal is further to establish a water-tight seal of the multi-purpose eyewear about the eye.

38. The multi-purpose eyewear of claim 33 wherein the frame has a predetermined shape and is conformable to a shape of the wearer's head to facilitate provision of an air-tight seal of the multi-purpose eyewear about the wearer's eye.

39. The multi-purpose eyewear of claim 33 wherein the frame comprises a mount to releasably attach the strap to the frame.

40. The multi-purpose eyewear of claim 39 wherein the strap further includes a connector attached to an end of the strap to releasably interconnect with the mount.

41. The multi-purpose eyewear of claim 40, wherein:
the strap has two ends selectively attachable to and detachable from the frame;
the frame further comprises another mount to releasably attach the strap to the frame; and
the strap further includes another connector attached to an opposite end of the strap to releasably interconnect with the another mount.

42. The multi-purpose eyewear of claim 41, wherein:
the adjustment device includes two portions each to controllably vary the length of the strap and to connect a respective one of the mounts to a corresponding one of the connectors; and
the two portions are operable independently of one another.

43. The multi-purpose eyewear of claim 40 wherein the adjustment device is to controllably vary the length of the strap and to connect the connector to the mount.

44. The multi-purpose eyewear of claim 43, wherein:
the adjustment device includes at least one of a screw and a threaded screw hole; and
the frame includes at least one of a threaded screw hole and a screw to respectively mate with the at least one of the screw and threaded screw hole.

45. The multi-purpose eyewear of claim 33, wherein the adjustment device includes at least one turnbuckle.

46. The multi-purpose eyewear of claim 33, wherein:
the cord comprises first and second sections; and
the adjustment device is to controllably vary the length of the strap by interconnecting an end of the first length of cord to an end of the second length of cord by a controllable varying distance.

47. The multi-purpose eyewear of claim 33 wherein the adjustment device is to controllably vary the length of the strap by varying a length of the cord.

48. The multi-purpose eyewear of claim 33, wherein the seal comprises:
a housing of a flexible material to conform to an irregular surface, the housing enclosing an interior space; and
a gel filling the interior space of the housing and being deformable in response to forcing the housing against the wearer's face for conforming to the wearer's face.

49. The multi-purpose eyewear of claim 33 further comprising two ear stems respectively attachable to the frame in place of the strap.

50. Multi-purpose eyewear comprising:
a frame being deformable from a first position to a second position, one of the first and second positions being a position in which the eyewear is appropriately used as at least one of eyeglasses and sunglasses, the other of the first and second positions being a position in which the eyewear is appropriately used as goggles; and
a tensioning device for selectively deforming the frame from one of the positions to the other.

* * * * *